US010151909B2

(12) United States Patent
Weber

(10) Patent No.: US 10,151,909 B2
(45) Date of Patent: Dec. 11, 2018

(54) SURGICAL MICROSCOPE AND METHOD FOR HIGHLIGHTING EYE LENS PIECES

(71) Applicant: CARL ZEISS MEDITEC AG, Jena (DE)

(72) Inventor: Lauric Weber, Aalen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 15/000,106

(22) Filed: Jan. 19, 2016

(65) Prior Publication Data

US 2016/0206198 A1 Jul. 21, 2016

(30) Foreign Application Priority Data

Jan. 20, 2015 (DE) .......................... 10 2015 100 765

(51) Int. Cl.
A61B 3/10 (2006.01)
A61B 3/14 (2006.01)
(Continued)

(52) U.S. Cl.
CPC ............ *G02B 21/22* (2013.01); *A61B 3/0008* (2013.01); *A61B 3/0025* (2013.01); *A61B 90/20* (2016.02); *G02B 21/0012* (2013.01)

(58) Field of Classification Search
CPC ....... A61B 3/0008; A61B 3/0025; A61B 3/13; A61B 3/132; A61B 3/14; G02B 21/0012; G02B 21/18; G02B 21/20; G02B 21/22
(Continued)

(56) References Cited

U.S. PATENT DOCUMENTS 4,786,155 A * 11/1988 Fantone ................. G02B 21/06 348/79
5,865,829 A * 2/1999 Kitajima .............. A61B 3/1241 359/351
(Continued)

FOREIGN PATENT DOCUMENTS

DE 102 42 983 A1 3/2004
DE 103 04 267 A1 8/2004
DE 10 2009 053 208 A1 8/2011

OTHER PUBLICATIONS

German Office Action dated Sep. 16, 2015.

*Primary Examiner* — Nicholas R Pasko
(74) *Attorney, Agent, or Firm* — Nixon Peabody LLP; Jeffrey L. Costellia

(57) ABSTRACT

A surgical microscope is disclosed with an observation beam path for generating an optical image from the eye, an illumination device for illuminating the eye, wherein the illumination device is designed for illuminating the eye with illumination light that contrasts eye lens pieces, in order to generate an optical contrast image that contrasts the eye lens pieces as optical image from the eye by means of the observation beam path, at least one digital camera, to which the optical contrast image is fed and which creates a digital contrast image from the optical contrast image and outputs it, an image processing unit, which is connected to the digital camera for receiving the digital contrast image and which is designed to find locations of increased contrast in the digital contrast image and to generate and output a superimposition image representing the locations of increased contrast, and a superimposing device.

15 Claims, 3 Drawing Sheets

Figure 1:
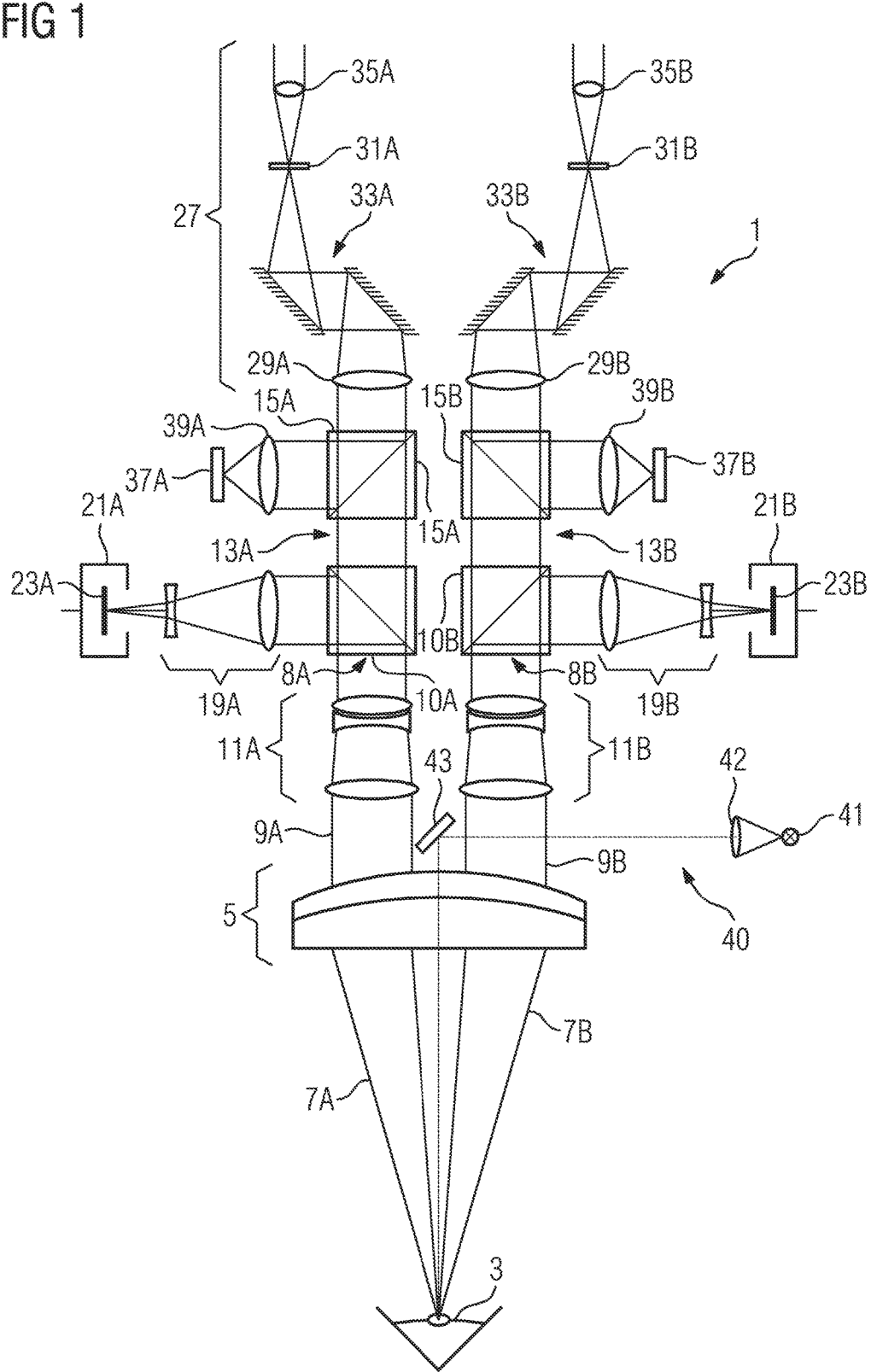

(51) Int. Cl.
*G02B 21/22* (2006.01)
*G02B 21/00* (2006.01)
*A61B 3/00* (2006.01)
*A61B 90/20* (2016.01)

(58) Field of Classification Search
USPC ........ 351/206, 221; 359/368, 372, 374, 375, 359/376, 377, 385, 389, 390
See application file for complete search history.

(56) References Cited

U.S. PATENT DOCUMENTS

| | | | |
|---|---|---|---|
| 6,227,667 B1 * | 5/2001 | Halldorsson | G02B 27/017 351/206 |
| 7,307,785 B2 * | 12/2007 | Obrebski | G02B 21/0012 359/388 |
| 8,189,201 B2 * | 5/2012 | Haisch | A61B 5/0066 356/497 |
| 8,328,358 B2 * | 12/2012 | Sander | A61B 3/132 351/221 |
| 8,427,743 B2 * | 4/2013 | Sander | G02B 21/0012 359/353 |
| 8,486,085 B2 * | 7/2013 | Moeller | A61B 3/107 351/211 |
| 2004/0061932 A1 | 4/2004 | Pensel et al. | |
| 2004/0169922 A1 * | 9/2004 | Wilson | G02B 21/22 359/462 |
| 2004/0227989 A1 | 11/2004 | Obrebski et al. | |
| 2012/0056996 A1 * | 3/2012 | Sander | G02B 21/16 348/47 |
| 2013/0150840 A1 * | 6/2013 | Sander | A61B 3/13 606/6 |

* cited by examiner

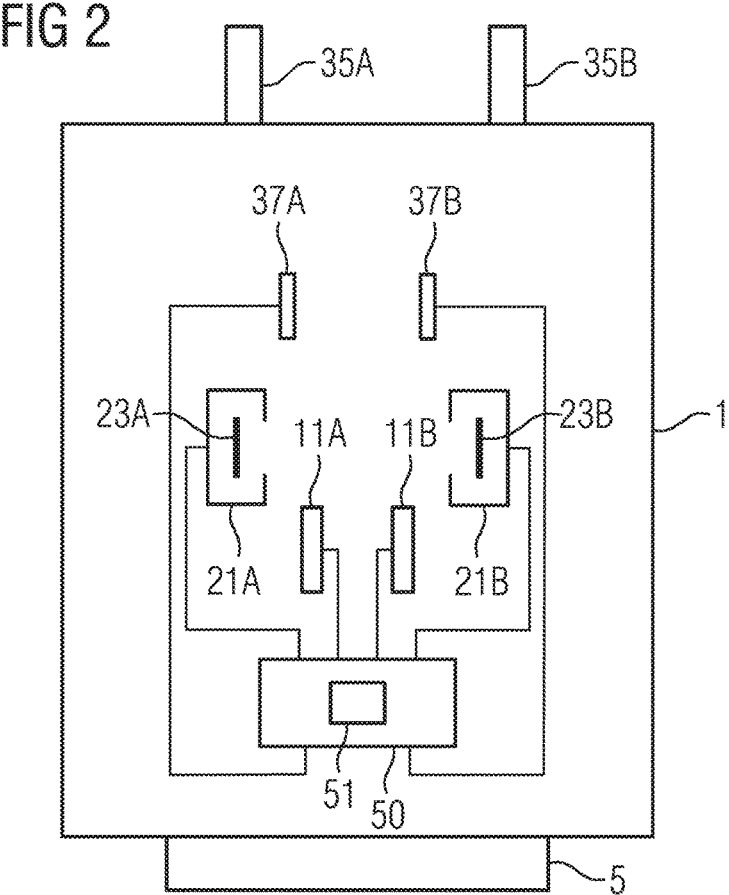
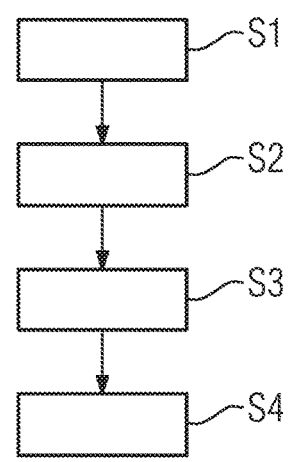

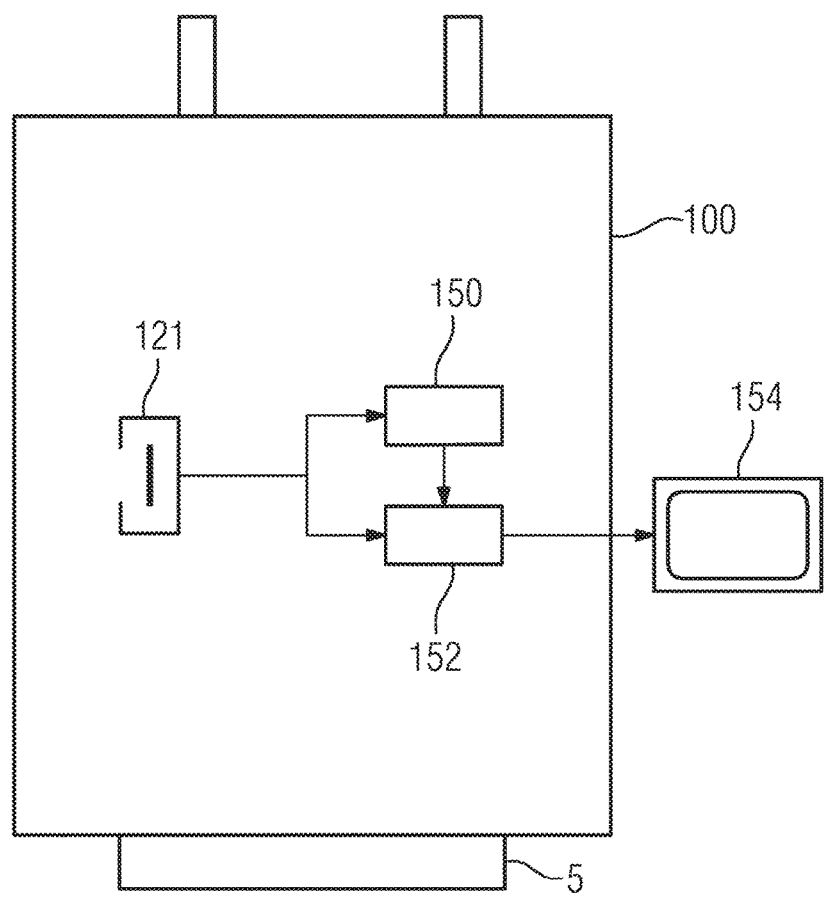

SURGICAL MICROSCOPE AND METHOD FOR HIGHLIGHTING EYE LENS PIECES

The present invention relates to a method for highlighting eye lens pieces in an image obtained from an eye by means of a surgical microscope. In addition, the invention relates to a surgical microscope suitable for carrying out said method.

In cataract operations, cloudy eye lenses are removed and replaced by intraocular lenses. The eye lens consists of a lens capsule and a lens core. During the cataract operation, the lens core is comminuted and extracted and the intraocular lens is inserted into the remaining lens capsule. In this case, the comminution and extraction are carried out e.g. by means of a small tube whose tip vibrates at an ultrasonic frequency, whereby the lens core is disintegrated, such that the debris can be extracted. This method is known as phacoemulsification. The lens core can also be disintegrated by means of a laser instead of by means of ultrasound. In the case of very soft cataracts, the extraction can even occur without disintegration of the lens core, under certain circumstances. In order to make the lens pieces visible during phacoemulsification, an illumination that contrasts the lens pieces is generally effected, such as, for example, a so-called red reflex illumination, in which the retina is illuminated and the red reflex light reflected from the retina causes the transparent lens pieces to appear in a contrasted way. Although the eye lens pieces are represented in a contrasted way by means of red reflex illumination, the contrast is sometimes weak, such that the lens pieces are not readily discernible, in particular but not exclusively to surgeons having poor vision.

DE 10 2009 053 208 A1 discloses an apparatus for monitoring the implantation of an intraocular lens. In said apparatus, an image processing apparatus in conjunction with a surgical microscope serves to overcome problems in association with the poor visual discernibility of the lens capsule after the removal of the lens core and of the intraocular lens during a cataract operation. By means of the image processing apparatus and a human-machine interface, information regarding quality assurance in respect of the actions of the operating physician are communicated to the latter. For this purpose, warning signals or direction arrows which the direction in which the physician is permitted to rotate or move the instrument or the intraocular lens can be superimposed.

It is an object of the present invention to provide a method and a surgical microscope which make it possible, in the image of the surgical microscope, to represent lens pieces during the disintegration of the lens in a manner readily discernible to the treating physician.

This object is achieved by means of a method for highlighting eye lens pieces as claimed in claim 1 and by means of a surgical microscope as claimed in claim 9. The dependent claims contain advantageous configurations of the invention.

The invention provides a method for the highlighted representation of eye lens pieces, i.e. pieces of the eye lens core, in an image obtained from an eye by means of a surgical microscope. In this case, the surgical microscope comprises at least one observation beam path for generating an optical image from the eye, an illumination device for illuminating the eye, at least one digital camera for recording the optical image from the eye, and an image processing unit. In the method, the eye is illuminated with illumination light that contrasts the eye lens pieces with the aid of the illumination device, in order to generate an optical contrast image that contrasts the eye lens pieces as optical image from the eye by means of the observation beam path. The optical contrast image is recorded by means of the at least one digital camera and converted into a digital contrast image. Locations of increased contrast are found in the digital contrast image with the aid of the image processing unit, and the image processing unit generates a superimposition image which represents the locations of increased contrast and which is adapted in its size at least to the optical contrast image or the digital contrast image. Said superimposition image is superimposed on at least the optical contrast image or the digital contrast image. At least the optical contrast image superimposed with the superimposition image or the digital contrast image superimposed with the superimposition image is output as the image obtained from the eye by means of the surgical microscope.

By means of the method according to the invention, pieces of the eye lens can be readily discerned by the treating surgeon during a cataract operation even if the illumination that contrasts the eye lens pieces, such as a red reflex illumination, for instance, leads only to a weak contrast. This considerably facilitates the cataract operation for the treating surgeon, in particular for surgeons having poor vision.

The at least one observation beam path can lead to at least one eyepiece of the surgical microscope. In this case, the superimposition image can be superimposed on the optical contrast image with the aid of at least one reflecting-in device in the observation beam path leading to the at least one eyepiece, such that the eye lens pieces are highlighted in the eyepiece image. In this case, the at least one eyepiece can be a purely optical eyepiece which enables direct viewing of the image of the eye superimposed with the superimposition image, or an electronic eyepiece which enables the image to be represented with the aid of a monitor, smartglasses or the like.

Typically, a surgical microscope is embodied as a stereomicroscope and therefore has two eyepieces. In this case, in particular, two cameras and two superimposition devices can also be present, namely respectively one camera and one superimposition device for each stereoscopic partial beam path of the stereomicroscope. The observation beam path then comprises a first stereoscopic partial beam path, which leads to a first eyepiece, and a second stereoscopic partial beam path, which leads to a second eyepiece. In this case, the optical contrast image is a stereoscopic optical contrast image having a first optical contrast partial image and a second contrast partial image. In each of the stereoscopic partial beam paths the respective optical contrast partial image is recorded by means of a digital camera, which creates a first and second digital contrast partial image, respectively, from the respective optical contrast partial image. The image processing unit then finds locations of increased contrast in the first digital contrast partial image and in the second digital contrast partial image, generates a first superimposition partial image representing the locations of increased contrast in the first digital contrast partial image and a second superimposition partial image representing the locations of increased contrast in the second digital contrast partial image, and outputs the first superimposition partial image and the second superimposition partial image. In this case, the first superimposition partial image and the second superimposition partial image are adapted in their size to the first optical contrast partial image and the second optical contrast partial image and together form a stereoscopic superimposition image. The first superimposition partial image is superimposed on the first optical contrast partial image in the first stereoscopic observation partial beam path by means of a first reflecting-in device for reflecting in image information, and the second superimposition partial image is superimposed on the second optical contrast partial image in the second stereoscopic observation partial beam path by means of a second reflecting-in device for reflecting in image information. The first optical contrast partial image superimposed with the first superimposition partial image and the second optical contrast partial image superimposed with the second superimposition partial image are output as a stereoscopic image obtained from the eye by means of the surgical microscope. In this way, a spatial image with highlighted eye lens pieces can be presented to the treating physician.

If superimposition of the superimposition image or of the superimposition partial images into the optical contrast image or into the optical contrast partial images is not desired or is not possible, e.g. owing to the lack of a reflecting-in device in the observation beam path, the superimposition image can be superimposed on the digital contrast image with the aid of an electronic superimposing unit. It goes without saying that this electronic superimposition is also possible if the superimposition image or the superimposition partial images is or are superimposed into the optical contrast image or into the optical contrast partial images, e.g. for documentation purposes or if a cataract operation is reproduced on an external monitor for teaching purposes.

In particular, light reflected from the retina can serve as illumination light that contrasts the eye lens pieces. This type of illumination is also called red reflex illumination because essentially the retina is illuminated by means of an illumination device of the surgical microscope and the reddish light reflected back from the retina then contrasts the eye lens pieces. An illumination device which enables a so-called 0° illumination or a so-called coaxial illumination is generally used for this purpose. In the case of 0° illumination, the illumination is effected substantially along the optical axis of the main objective of the microscope or at a very small angle with respect thereto (max. 6°), as a result of which even deep operation channels can be illuminated and, in particular, illumination of the retina through the pupil of the eye is made possible. In coaxial illumination, the illumination is effected along the optical axis of the two stereoscopic observation partial beam paths, which likewise enables the illumination of deep operation channels and thus the illumination of the retina through the pupil of the eye.

For finding the locations of increased contrast, a high-pass filter, in particular, can be used in the image processing unit. A high-pass filter makes it possible to find edges in the image, i.e. locations having great differences in brightness. In this case, a threshold value for the intensity difference is typically set, which has to be exceeded in order to identify the edge as such. In this way, it is possible to find the margins of eye lens pieces, which can then be represented in the superimposition image. In this case, the locations of increased contrast can be represented in the superimposition image by virtue of the fact that the edges are highlighted in color, for example, or the areas enclosed by the edges are highlighted in color.

Since only an improved representation of the eye lens pieces is intended to be effected, it suffices for the locations of increased contrast to be found in the region of the pupil of the eye, that is to say where the eye lens pieces are situated. In one advantageous development of the method according to the invention, the image processing unit can subdivide the contrast image into a central region corresponding to the pupil of the eye and a marginal region surrounding the pupil of the eye. In this case, the locations of increased contrast are found only in the central region, that is to say in the region of the image corresponding to the pupil. The processing complexity can be reduced as a result. Moreover, highlightings by means of the superimposition image which do not correspond to eye lens pieces can be avoided.

A surgical microscope according to the invention for generating an image from an eye, wherein eye lens pieces are highlighted in the image, comprises an observation beam path for generating an optical image from the eye, and an illumination device for illuminating the eye. The illumination device is designed for illuminating the eye with illumination light that contrasts eye lens pieces, in order to generate an optical contrast image that contrasts the eye lens pieces as optical image from the eye by means of the observation beam path. It can be configured, for example, in such a way that it enables a 0° illumination and/or a coaxial illumination, such that a red reflex illumination can be realized. Furthermore, the illumination device can additionally also enable an oblique illumination i.e. an illumination in which the optical axis of the illumination beam path forms an angle of greater than 6° with the optical axis of the main objective, in order to be able to illuminate the surroundings of the operation site.

Moreover, the surgical microscope according to the invention comprises at least one digital camera, to which the optical contrast image is fed and which creates a digital contrast image from the optical contrast image and outputs it. An image processing unit is connected to the digital camera for receiving the digital contrast image, said image processing unit being designed to find locations of increased contrast in the digital contrast image and also to generate and output a superimposition image representing the locations of increased contrast. In this case, the superimposition image is adapted in its size to the digital contrast image or the optical contrast image.

The surgical microscope according to the invention additionally comprises at least one superimposing device for superimposing the optical contrast image or the digital contrast image with the superimposition image and for outputting the optical contrast image superimposed with the superimposition image or the digital contrast image superimposed with the superimposition image as the image from the eye in which eye lens pieces are highlighted.

The surgical microscope according to the invention makes it possible to carry out the method according to the invention, such that the properties and advantages described with regard to the method according to the invention can be realized with the surgical microscope according to the invention.

In the surgical microscope according to the invention, the observation beam path can lead to at least one eyepiece. In this case, the superimposing device can comprise a reflecting-in device for reflecting image information into the observation beam path, wherein the reflecting-in device, for receiving the superimposition image, is connected to the image processing unit and is designed to superimpose the received superimposition image on the optical contrast image in the observation beam path leading to the at least one eyepiece. In this way, it is possible to highlight the eye lens pieces in the image viewed with the at least one eyepiece image. In this case, the at least one eyepiece can be a purely optical eyepiece or an electronic eyepiece, as has been explained with regard to the method according to the invention.

In order that the superimposition image does not disturb the processing of the optical contrast image recorded by means of the at least one camera, the at least one camera can be arranged in the at least one observation beam path in such a way that it records the optical contrast image without the superimposed superimposition image. For this purpose, the camera can be arranged upstream of the reflecting-in device in the observation beam path. In the case where two observation beam paths are present, there is also the possibility of arranging the camera in one observation beam path and of arranging the reflecting-in device in the other observation beam path.

The surgical microscope according to the invention can be a stereomicroscope, in particular. In this case, the observation beam path comprises a first stereoscopic partial beam path, which leads to a first eyepiece, and a second stereoscopic partial beam path, which leads to a second eyepiece. The optical contrast image is then a stereoscopic optical contrast image having a first optical contrast partial image and a second contrast partial image. Moreover, in each of the stereoscopic partial beam paths a digital camera is then arranged, to which the respective optical contrast partial image is fed and which creates a first and second digital contrast partial image, respectively, from the respective optical contrast partial image. Moreover, the image processing unit is designed to find locations of increased contrast in the digital contrast partial images and also to generate and output a first superimposition partial image representing the locations of increased contrast in the first digital contrast partial image and a second superimposition partial image representing the locations of increased contrast in the second digital contrast partial image, wherein the first superimposition partial image and the second superimposition partial image are adapted in their size to the first optical contrast partial image and the second optical contrast partial image, respectively, and together form a stereoscopic superimposition image. The superimposing device then comprises a first reflecting-in device for reflecting image information into the first stereoscopic observation partial beam path and a second reflecting-in device for reflecting image information into the second stereoscopic observation partial beam path, wherein the first reflecting-in device is connected to the image processing unit for the purpose of receiving the first superimposition partial image and the second reflecting-in device is connected to said image processing unit for the purpose of receiving the second superimposition partial image. The first reflecting-in device is designed to superimpose the received first superimposition partial image on the first optical contrast partial image in the first stereoscopic observation partial beam path and the second reflecting-in device is designed to superimpose the received second superimposition partial image on the second optical contrast partial image in the second stereoscopic observation partial beam path. Such a surgical microscope makes it possible to present a spatial image with highlighted eye lens pieces to a treating physician.

If superimposition of the superimposition image or of the superimposition partial images into the optical contrast image or into the optical contrast partial images is not desired or is not possible, e.g. owing to the lack of a reflecting-in device in the observation beam path, the superimposing device of the surgical microscope according to the invention can comprise an electronic superimposing unit for electronically superimposing the digital contrast image with the superimposition image. It goes without saying that this electronic superimposition is also possible if the superimposition image or the superimposition partial images is or are superimposed into the optical contrast image or into the optical contrast partial images, e.g. for documentation purposes or if a cataract operation is reproduced on an external monitor for teaching purposes.

For finding the locations of increased contrast, the image processing unit can comprise a high-pass filter, which can be used to find edges in the contrast image, as has been described with regard to the method according to the invention.

The image processing unit can additionally be designed to represent the locations of increased contrast in the superimposition image by regions highlighted in color or edges highlighted in color, as has already been described with regard to the method according to the invention.

The surgical microscope according to the invention can be embodied as a stereomicroscope, in particular, i.e. the observation beam path has two stereoscopic partial beam paths, each of which leads to a separate eyepiece. In this case, there is the possibility either of providing a camera and a reflecting-in device only in one of the two stereoscopic partial beam paths or of providing a camera and a reflecting-in device in each case in both stereoscopic partial beam paths.

Further features, properties and advantages of the present invention will become apparent from the following description of exemplary embodiments with reference to the accompanying figures.

FIG. 1 substantially shows the optical components of a first exemplary embodiment of a surgical microscope according to the invention.

FIG. 2 substantially shows the electronic components of a first exemplary embodiment of a surgical microscope according to the invention.

FIG. 3 shows, on the basis of a flow diagram, one exemplary embodiment of the highlighting of eye lens pieces in an image obtained by means of the surgical microscope.

FIG. 4 substantially shows the electronic components of a second exemplary embodiment of a surgical microscope according to the invention.

FIGS. 1 and 2 show, in a schematic illustration, a first exemplary embodiment of a surgical microscope 1 according to the invention, such as can be used in cataract operations. In this case, FIG. 1 substantially shows the optical components of the surgical microscope 1 and FIG. 2 substantially shows the electronic components.

The surgical microscope 1 illustrated comprises an objective 5, which is to be directed toward an observation object 3 and which, in the present example, is illustrated as an achromatic lens constructed from at least two partial lenses cemented to one another. The object field 3, which lies in the eye lens in the present case, is arranged in the focal plane of the objective 5, such that it is imaged to infinity, that is to say that a divergent beam 7 emerging from the observation object 3 is converted into a parallel beam 9 upon passing through the objective 5.

Instead of just one achromatic lens, as is used as the objective 5 in the present example, it is also possible to use an objective lens system comprising a plurality of individual lenses, for instance a so-called varifocal objective, which can be used to vary the back focus of the surgical microscope 1, i.e. the distance between the focal plane and the objective 5. By varying the back focus, it is possible to adapt a surgical microscope 1 with varifocal objective to different working distances, without the position of the surgical microscope itself needing to be altered. In such a varifocal system, too, the object field 3 arranged in the focal plane is imaged to infinity, such that a parallel beam is present on the observer side in the case of a varifocal objective, too.

A magnifying apparatus 11A, 11B is arranged on the observer side of the objective 5, which magnifying apparatus can be embodied either as a zoom system for changing the magnification factor in a continuously variable manner as in the example illustrated, or as a so-called Galilean changer for changing the magnification factor in a stepwise manner. In a zoom system, illustrated by way of example as a lens combination having three lenses, the two object-side lenses can be displaced in order to vary the magnification factor. In actual fact, however, the zoom system can also have more than three lenses, for example four or more lenses, in which case both outer lenses can then be arranged in a fixed manner. In a Galilean changer, by contrast, there are a plurality of fixed lens combinations which represent different magnification factors and can be introduced into the beam path alternately. Both a zoom system and a Galilean changer convert an object-side parallel beam into an observer-side parallel beam having a different beam diameter. In this case, the magnifying apparatus 11A, 11B is often already part of the binocular beam path of the surgical microscope 1, that is to say it has a dedicated lens combination for each stereoscopic observation partial beam path of the surgical microscope 1.

Adjacent to the magnifying apparatus 11A, 11B on the observer side there is an output coupling arrangement 8A, 8B having beam splitter prisms 10A, 10B, with the aid of which, from each stereoscopic partial beam 9A, 9B, a part is respectively coupled out and forwarded to a camera 21A, 21B having a digital image sensor 23A, 23B, said camera being connected to the corresponding partial beam path of the surgical microscope 1. The cameras 21A, 21B, which are coupled to the output coupling arrangement 8A, 8B with the interposition of camera adapters 19A, 19B, which effect a focal length adaptation, are connected to an image processing unit 50 (see FIG. 2), to which digital images generated by means of the image sensors 23A, 23B are output. In the present exemplary embodiment, the image processing unit 50 comprises a high-pass filter 51 for the purpose of evaluating the digital images. The evaluation of the digital images will be explained later with reference to FIG. 3. In the present exemplary embodiment, the image processing unit 50 is additionally connected to the controller of the magnifying apparatus 11A, 11B in order to be able to receive the set magnification factor therefrom.

The surgical microscope 1 additionally comprises displays 37A, 37B, on which superimposition images for superimposition into the observation partial beam paths can be represented. In the present case, the superimposition images are generated by the image processing unit 50, to which the displays 37A, 37B are coupled. Each display 37A, 37B is assigned a superimposition optical unit 39A, 39B and a beam splitter prism 15A, 15B of an input coupling arrangement 13A, 13B, with the aid of which a beam emerging from a display 37A, 37B and representing a superimposition image can be superimposed on the corresponding stereoscopic partial beam 9A, 9B in that part of the observation beam path of the surgical microscope 1 which leads to a binocular tube 27.

The binocular tube 27, which is adjacent to the input coupling arrangement 13A, 13B on the observer side, has two tube objectives 29A, 29B, which focus the respective parallel beam 9A, 9B onto an intermediate image plane 31A, 31B, that is to say image the observation object 3 onto the respective intermediate image plane 31A, 31B. The intermediate images situated in the intermediate image planes 31A, 31B are finally focused in turn to infinity by eyepiece lenses 35A, 35B, such that a surgeon can observe the intermediate image with a relaxed eye. Moreover, a magnification of the distance between the two partial beams 9A, 9B is carried out in the binocular tube by means of a mirror system or by means of prisms 33A, 33B in order to adapt said distance to the intraocular distance of the observer. In addition, image erection is carried out by the mirror system or the prisms 33A, 33B.

The surgical microscope 1 is also equipped with an illumination device 40, by means of which the observation object 3 can be illuminated with illumination light. For this purpose, the illumination device has a light source 41, for instance a halogen incandescent light, a gas discharge lamp such as a xenon lamp, for example, one or more LEDs, etc. The light source 41 can be arranged directly at the surgical microscope 1 or in a manner remote from the surgical microscope 1, for instance the microscope stand. In the case of a remote arrangement, the light from the light source 41 is guided to the surgical microscope 1 by means of an optical waveguide.

The light originating from the light source 41 is directed in the direction of the eye 3 via a deflection mirror 43. In order to enable a red reflex illumination of the eye lens, in which the retina is illuminated with illumination light that is then reflected from the retina substantially in the red spectral range and thus illuminates the eye lens from the fundus of the eye with reddish light, the illumination beam path in the surgical microscope shown in FIG. 1 is embodied as so-called 0° illumination. In the case of such illumination, the illumination beam path is coupled into the main objective 5 in the direction of the eye 3 by means of the deflection mirror 43 between the two partial beam paths 9A, 9B, through the objective 5 along the optical axis of the objective 5—or at an angle of less than 6° with respect to the optical axis of the objective 5. On account of the small angle with respect to the optical axis of the main objective 5, the illumination light can pass through the pupil of the eye to the retina during the observation of the eye lens. Additionally or alternatively, an illumination beam path which enables a so-called coaxial illumination can also be present. In coaxial illumination, a first illumination partial beam path and a second illumination partial beam path are present, which are coupled into the surgical microscope via one or a plurality of beam splitters coaxially or at a small angle (less than 6°) with respect to the optical axes of the observation partial beam paths, that is to say coaxially with the stereoscopic partial beams 9A, 9B. As with 0° illumination, a red reflex illumination of the eye lens can be realized with coaxial illumination, too. With the aid of the red reflex illumination, eye lens pieces are represented with higher contrast in comparison with a conventional illumination in the image obtained by means of the surgical microscope during a phacoemulsification. In order to avoid damage to the retina by a focused illumination, the illumination device 40 contains an illumination optical unit 42 which provides for a slightly defocused illumination of the retina of the eye 3.

In addition, an illumination beam path embodied as so-called oblique illumination can also be realized in the surgical microscope. In such oblique illumination, the beam path runs at a relatively large angle (6° or more) with respect to the optical axis of the objective 5 and can run completely outside the objective 5. Alternatively, however, there is also the possibility of allowing the illumination beam path of the oblique illumination to run through a marginal region of the objective 5. With oblique illumination, e.g. the surroundings of the operation site can be illuminated during a phacoemulsification.

One exemplary embodiment of the method according to the invention for highlighting eye lens pieces in the image of the surgical microscope 1 is described below with reference to the flow diagram from FIG. 3.

The method is carried out while the eye lens or the eye lens parts is or are illuminated by means of a red reflex illumination during the phacoemulsification, that is to say while the eye is illuminated with illumination light that contrasts the eye lens parts. In a first step S1, during the red reflex illumination or some other illumination suitable for contrasting eye lens tissue, an image from the eye, referred to as contrast image hereinafter, is recorded by means of the image sensor 23A, 23B of at least one of the cameras 21A, 21B, and is then output as a digital contrast image to the image processing unit 50.

In step S2, a suitable algorithm which can be used to find locations of increased contrast in the digital contrast image is employed in the image processing unit 50. In the present exemplary embodiment, the algorithm is realized in the form of a high-pass filter 51, which finds edges in the image, that is to say locations at which high differences in brightness meet one another. If the high-pass filter 51 is used, the image processing unit can register a difference in brightness as an edge if the difference in brightness exceeds a specific predefined threshold value. In red reflex illumination, eye lens parts are represented in a contrasted fashion, that is to say that differences in brightness with respect to the surroundings occur at their edges in the recorded image. The edges found by means of the high-pass filter, that is to say the locations of increased contrast, therefore represent the margins of the eye lens parts.

On the basis of the found locations of increased contrast, the image processing unit 50 then generates a superimposition image for the display 37A, 37B situated in the same stereoscopic partial beam path as the camera 21A, 21B which recorded the contrast image. It should be noted at this juncture that it is sufficient if a contrast image is recorded in one of the two stereoscopic partial beam paths, in which contrast image the locations of increased contrast are then found by means of the high-pass filter 51, and the image processing unit generates a superimposition image for the display in the corresponding partial beam path on the basis of the found locations of increased contrast. If the eye lens parts are also intended to be highlighted stereoscopically, by contrast, a stereoscopic contrast partial image is recorded in each of the two partial beam paths and a superimposition partial image is generated on the basis of the recorded contrast partial image for each partial beam path. The two superimposition partial images then jointly form a stereoscopic superimposition image.

The superimposition image generated in step S3 can contain colored markings, for example, which represent the edges detected by the high-pass filter 51. In this case, the superimposition image shows the contours of the eye lens pieces. Since the eye lens pieces are generally surrounded by closed edges, there is also the possibility of coloring the areas enclosed by the edges in the superimposition image. In both cases, the generated superimposition image is adapted in size and position to the contrast image obtained during the red reflex illumination by means of the surgical microscope and is output to the display 37A, 37B of the corresponding stereoscopic partial beam path. In this case, the size of the superimposition image can be adapted on the basis of the zoom factor received from the controller of the zoom system.

In step S4, the superimposition image is then represented on the display and superimposed on the contrast image obtained by means of the surgical microscope by means of the superimposition optical unit 39A, 39B and the beam splitter prism 15A, 15B of the corresponding stereoscopic partial beam path. A superimposition of the purely optically generated contrast image and the superimposition image is therefore present in that part of the stereoscopic partial beam path which leads to the eyepiece tube 27, such that an image in which the eye lens pieces are artificially highlighted can be viewed at the corresponding eyepiece 35A, 35B. This makes it easier for the treating surgeon to find and remove the eye lens pieces.

In order to restrict the finding of locations of increased contrast to the region of interest in the eye, that is to say the region in which the eye lens is situated, there is optionally the possibility of subdividing the digital contrast image into a central region corresponding to the pupil of the eye and a marginal region surrounding the pupil of the eye by means of the image processing unit 50. Finding the locations of increased contrast then need only be carried out in the central region.

FIG. 4 shows, in a schematic illustration, essentially the electronic components of a second exemplary embodiment of a surgical microscope 101 according to the invention, such as can be used in cataract operations. The optical components and the camera(s) may correspond to those in the first exemplary embodiment and will therefore not be explained again.

In the second exemplary embodiment, in accordance with the method described with reference to FIG. 3, a superimposition image for highlighting eye lens pieces is generated with the aid of an imaging processing unit 150, which corresponds to the image processing unit in the first exemplary embodiment, on the basis of a contrast image recorded by means of a camera 121. In contrast to the first exemplary embodiment, however, the superimposition image is not superimposed on an optical contrast image, but rather on the digital contrast image. For this purpose, the surgical microscope 101 comprises an electronic superimposing unit 152, which is connected to the camera 121 for receiving the digital contrast image and to the image processing unit 150 for receiving the superimposition image and in which the superimposition image is electronically superimposed on the digital contrast image. The digital contrast image superimposed with the superimposition image is then forwarded to a monitor 154, on which it is represented. Alternatively or additionally, the digital contrast image superimposed with the superimposition image can also be forwarded to a recorder for storage (e.g. for documentation purposes).

As in the first exemplary embodiment, in the second exemplary embodiment, too, there is the possibility of the image processing unit 150 subdividing the digital contrast image into a central region corresponding to the pupil of the eye and a marginal region surrounding the pupil of the eye, in order to restrict the finding of locations of increased contrast to the region of interest in the eye, that is to say the region in which the eye lens is situated.

The electronic superimposing unit 152 can be present in addition to the displays 37A, 37B and beam splitter prisms 15A, 15B which were described with regard to the first exemplary embodiment and with which the superimposition image or the superimposition partial images is or are superimposed on the optical contrast image or the optical contrast partial images in the observation beam path, for example in order, during a cataract operation, to represent images of the eye with highlighted eye lens pieces on a monitor as well for teaching purposes or in order, during a cataract operation, to record images of the eye with highlighted eye lens pieces for documentation purposes. Alternatively, the electronic superimposing unit 152 can also be used if no displays 37A, 37B and beam splitter prisms 15A, 15B are present in the surgical microscope 101. A treating physician can then verify whether he has acquired all eye lens pieces during the operation, by looking at the monitor.

The present invention has been described in greater detail on the basis of exemplary embodiments for explanation purposes. A person skilled in the art recognizes, however, that deviations from the exemplary embodiments described are possible. In this regard, the first exemplary embodiment contains an input coupling device 13A, 13B and an output coupling device 8A, 8B, in the case of which their arrangement ensures that the superimposition image is not concomitantly recorded by the cameras 21A, 21B. However, surgical microscopes also exist in which a large beam splitter cube extending over both stereoscopic partial beam paths is present and is used to carry out both the input coupling of images represented on displays into the stereoscopic partial beam paths and the output coupling of partial beam paths to cameras. In this case, the stereoscopic partial images superimposed with the superimposition images are fed to the cameras. In this case, it should be ensured by means of suitable measures that the superimposition images are not recorded by the cameras, since otherwise the evaluation by the image processing unit would be disturbed. Moreover, instead of the beam splitter prisms, other types of beam splitters, for example partly transmissive mirrors, can be used in the output coupling arrangement and/or the input coupling arrangement. Therefore, the invention is not intended to be restricted to specific combinations of features of the exemplary embodiment, but rather only by the appended claims.

1 Surgical microscope
3 Observation object/eye
5 Objective
7 Beam
8A,B Output coupling device
9A,B Partial beam path
10A,B Beam splitter prism
11A,B Magnifying apparatus
13A,B Input coupling device
15A,B Beam splitter prism
19A,B Camera adapter
21A,B Camera
23A,B Image sensor
27 Binocular tube
29A,B Tube objectives
31A,B Intermediate image plane
33A,B Prism
35A,B Eyepiece lens
37A,B Display
39A,B Superimposition optical unit
40 Illumination device
41 Light source
42 Illumination optical unit
43 Deflection mirror
50 Image processing unit
51 High-pass filter
101 Surgical microscope
121 Camera
150 Image processing unit
152 Superimposing unit
154 Monitor
S1 Image recording
S2 Finding locations of increased contrast
S3 Generating a superimposition image
S4 Representing the superimposition image

The invention claimed is:

1. A method for a highlighted representation of eye lens pieces in an image obtained from an eye by means of a surgical microscope, wherein the surgical microscope comprises at least one observation beam path for generating an optical image from the eye an illumination device for illuminating the eye, at least one digital camera for recording the optical image from the eye, and an image processing unit, wherein the eye is illuminated with illumination light that contrasts the eye lens pieces with the aid of the illumination device, in order to generate an optical contrast image that contrasts the eye lens pieces as optical image from the eye by means of the observation beam path, wherein the illumination light that contrasts the eye lens pieces is light reflected from the retina and wherein the illumination light is projected at 6° or less along the optical axis of the at least one observation beam path or along the optical axis of the main objective of the microscope in order to generate an illumination of the eye lens, in which the retina is illuminated with illumination light that is then reflected from the retina in the red spectral range and thus illuminates the eye lens from the fundus of the eye with light with a wavelength of between 620 and 750 nm, the optical contrast image is recorded by means of the at least one digital camera and converted into a digital contrast image, locations of increased contrast are found in the digital contrast image with the aid of the image processing unit, wherein an algorithm is employed in the image processing unit, which algorithm is used to find locations of increased contrast by finding edges in the digital contrast image, the image processing unit generates a superimposition image which represents the locations of increased contrast and which is adapted in its size at least to the optical contrast image or the digital contrast image, the superimposition image is superimposed on at least the optical contrast image or the digital contrast image, and at least the optical contrast image superimposed with the superimposition image or the digital contrast image superimposed with the superimposition image is output as the image obtained from the eye by means of the surgical microscope.

2. A surgical microscope for generating an image from an eye, wherein eye lens pieces are highlighted in the image, comprising an observation beam path for generating an optical image from the eye, an illumination device for illuminating the eye, wherein the illumination device is designed for illuminating the eye with illumination light that contrasts eye lens pieces, in order to generate an optical contrast image that contrasts the eye lens pieces as optical image from the eye by means of the observation beam path and wherein the illumination light is projected at 6° or less along the optical axis of the observation beam path or along the optical axis of the main objective of the microscope in order to generate an illumination of the eye lens, in which the retina is illuminated with illumination light that is then reflected from the retina in the red spectral range and thus illuminates the eye lens from the fundus of the eye with light with a wavelength of between 620 and 750 nm, at least one digital camera, to which the optical contrast image is fed and which creates a digital contrast image from the optical contrast image and outputs it, an image processing unit, which is connected to the digital camera for receiving the digital contrast image and which is designed to find locations of increased contrast in the digital contrast image and to generate and output a superimposition image representing the locations of increased contrast, wherein the superimposition image is adapted in its size to the digital contrast image or the optical contrast image, wherein an algorithm is employed in the image processing unit, which algorithm is used to find locations of increased contrast by finding edges in the digital contrast image, and at least one superimposing device for superimposing the optical contrast image or the digital contrast image with the superimposition image and for outputting the optical contrast image superimposed with the superimposition image or the digital contrast image superimposed with the superimposition image as the image from the eye in which eye lens pieces are highlighted.

3. A method for a highlighted representation of eye lens pieces in an image obtained from an eye by means of a surgical microscope, wherein the surgical microscope comprises at least one observation beam path for generating an optical image from the eye an illumination device for illuminating the eye, at least one digital camera for recording the optical image from the eye, and an image processing unit, wherein the eye is illuminated with illumination light that contrasts the eye lens pieces with the aid of the illumination device, in order to generate an optical contrast image that contrasts the eye lens pieces as optical image from the eye by means of the observation beam path, wherein the illumination light that contrasts the eye lens pieces is light reflected from the retina and wherein the illumination light is projected at 6° or less along the optical axis of the at least one observation beam path or along the optical axis of the main objective of the microscope in order to generate an illumination of the eye lens, in which the retina is illuminated with illumination light that is then reflected from the retina in the red spectral range and thus illuminates the eye lens from the fundus of the eye with light with a wavelength of between 620 and 750 nm, the optical contrast image is recorded by means of the at least one digital camera and converted into a digital contrast image, locations of increased contrast are found in the digital contrast image with the aid of the image processing unit, wherein an algorithm is employed in the image processing unit, which algorithm is used to find locations of increased contrast in the digital contrast image, the image processing unit generates a superimposition image which represents the locations of increased contrast and which is adapted in its size at least to the optical contrast image or the digital contrast image, the superimposition image is superimposed on at least the optical contrast image or the digital contrast image, and at least the optical contrast image superimposed with the superimposition image or the digital contrast image superimposed with the superimposition image is output as the image obtained from the eye by means of the surgical microscope.

4. The method as claimed in claim 3, wherein the superimposition image is superimposed on the digital contrast image with the aid of an electronic superimposing unit.

5. The method as claimed in claim 3, wherein the locations of increased contrast are represented in the superimposition image by regions highlighted in color or edges highlighted in color.

6. The method as claimed in claim 3, wherein the image processing unit subdivides the electronic contrast image into a central region corresponding to the pupil of the eye and a marginal region surrounding the pupil of the eye and finds the locations of increased contrast only in the central region.

7. The method as claimed in claim 3, wherein the observation beam path leads to at least one eyepiece of the surgical microscope, and the superimposition image is superimposed on the optical contrast image in the observation beam path leading to the at least one eyepiece with the aid of at least one reflecting-in device.

8. The method as claimed in claim 7, wherein the observation beam path comprises a first stereoscopic partial beam path, which leads to a first eyepiece, and a second stereoscopic partial beam path (9B), which leads to a second eyepiece, the optical contrast image is a stereoscopic optical contrast image having a first optical contrast partial image and a second contrast partial image, in each of the stereoscopic partial beam paths the respective optical contrast partial image is recorded by means of a digital camera, which creates a first and second digital contrast partial image, respectively, from the respective optical contrast partial image, the image processing unit finds locations of increased contrast in the first digital contrast partial image and the second digital contrast partial image and also generates and outputs a first superimposition partial image representing the locations of increased contrast in the first digital contrast partial image and a second superimposition partial image representing the locations of increased contrast in the second digital contrast partial image, wherein the first superimposition partial image and the second superimposition partial image are adapted in their size to the first optical contrast partial image and the second optical contrast partial image, respectively, and together form a stereoscopic superimposition image, and the first superimposition partial image is superimposed on the first optical contrast partial image in the first stereoscopic observation partial beam path by means of a first reflecting-in device for reflecting in image information, and the second superimposition partial image is superimposed on the second optical contrast partial image in the second stereoscopic observation partial beam path by means of a second reflecting-in device for reflecting in image information, and the first optical contrast partial image superimposed with the first superimposition partial image and the second optical contrast partial image superimposed with the second superimposition partial image are output as a stereoscopic image obtained from the eye by means of the surgical microscope.

9. A surgical microscope for generating an image from an eye, wherein eye lens pieces are highlighted in the image, comprising an observation beam path for generating an optical image from the eye, an illumination device for illuminating the eye, wherein the illumination device is designed for illuminating the eye with illumination light that contrasts eye lens pieces, in order to generate an optical contrast image that contrasts the eye lens pieces as optical image from the eye by means of the observation beam path and wherein the illumination light is projected at 6° or less along the optical axis of the observation beam path or along the optical axis of the main objective of the microscope in order to generate an illumination of the eye lens, in which the retina is illuminated with illumination light that is then reflected from the retina in the red spectral range and thus illuminates the eye lens from the fundus of the eye with light with a wavelength of between 620 and 750 nm, at least one digital camera, to which the optical contrast image is fed and which creates a digital contrast image from the optical contrast image and outputs it, an image processing unit, which is connected to the digital camera for receiving the digital contrast image and which is designed to find locations of increased contrast in the digital contrast image and to generate and output a superimposition image representing the locations of increased contrast, wherein the superimposition image is adapted in its size to the digital contrast image or the optical contrast image, wherein an algorithm is employed in the image processing unit, which algorithm is used to find locations of increased contrast in the digital contrast image, and at least one superimposing device for superimposing the optical contrast image or the digital contrast image with the superimposition image and for outputting the optical contrast image superimposed with the superimposition image or the digital contrast image superimposed with the superimposition image as the image from the eye in which eye lens pieces are highlighted.

10. The surgical microscope as claimed in claim 9, wherein the superimposing device comprises an electronic superimposing unit for electronically superimposing the digital contrast image with the superimposition image.

11. The surgical microscope as claimed in claim 9, wherein the illumination device additionally enables an oblique illumination wherein the oblique illumination is projected at an angle of 6° or more with respect to the optical axis of the main objective.

12. The surgical microscope as claimed in claim 9, wherein the image processing unit is designed to represent the locations of increased contrast in the superimposition image by regions highlighted in color or edges highlighted in color.

13. The surgical microscope as claimed in claim 9, wherein the observation beam path leads to at least one eyepiece, the superimposing device comprises a reflecting-in device for reflecting image information into the observation beam path, wherein the reflecting-in device, for receiving the superimposition image, is connected to the image processing unit and is designed to superimpose the received superimposition image on the optical contrast image in the observation beam path leading to the at least one eyepiece.

14. The surgical microscope as claimed in claim 13, wherein the reflecting-in device and the at least one camera are arranged in the same at least one observation beam path in such a way that it records the optical contrast image without the superimposed superimposition image by locating the at least one camera upstream of the reflecting-in device in the observation beam path.

15. The surgical microscope as claimed in claim 13, wherein the observation beam path comprises a first stereoscopic partial beam path, which leads to a first eyepiece, and a second stereoscopic partial beam path (9B), which leads to a second eyepiece, the optical contrast image is a stereoscopic optical contrast image having a first optical contrast partial image and a second contrast partial image, in each of the stereoscopic partial beam paths a digital camera is arranged, to which the respective optical contrast partial image is fed and which creates a first and second digital contrast partial image, respectively, from the respective optical contrast partial image, the image processing unit is designed to find locations of increased contrast in the digital contrast partial images and also to generate and output a first superimposition partial image representing the locations of increased contrast in the first digital contrast partial image and a second superimposition partial image representing the locations of increased contrast in the second digital contrast partial image, wherein the first superimposition partial image and the second superimposition partial image are adapted in their size to the first optical contrast partial image and the second optical contrast partial image, respectively, and together form a stereoscopic superimposition image, and the superimposing device comprises a first reflecting-in device for reflecting image information into the first stereoscopic observation partial beam path and a second reflecting-in device for reflecting image information into the second stereoscopic observation partial beam path, wherein the first reflecting-in device is connected to the image processing unit for the purpose of receiving the first superimposition partial image and the second reflecting-in device is connected to said image processing unit for the purpose of receiving the second superimposition partial image, the first reflecting-in device is designed to superimpose the received first superimposition partial image on the first optical contrast partial image in the first stereoscopic observation partial beam path and the second reflecting-in device is designed to superimpose the received second superimposition partial image on the second optical contrast partial image in the second stereoscopic observation partial beam path.

* * * * *